US005756748A

United States Patent [19]
Jaksch et al.

[11] Patent Number: 5,756,748
[45] Date of Patent: May 26, 1998

[54] PROCESS FOR THE PREPARATION OF SAMERIDINE

[75] Inventors: Peter Jaksch; Rune Sandberg, both of Järna, Sweden

[73] Assignee: Astra AB, Sweden

[21] Appl. No.: 612,967

[22] PCT Filed: Nov. 29, 1995

[86] PCT No.: PCT/SE94/01427

§ 371 Date: Mar. 7, 1996

§ 102(e) Date: Mar. 7, 1996

[87] PCT Pub. No.: WO96/19453

PCT Pub. Date: Jun. 27, 1996

[30] Foreign Application Priority Data

Dec. 21, 1994 [SE] Sweden ................................. 9404438

[51] Int. Cl.$^6$ ................ C07D 211/56; C07D 211/30; C07D 211/32; C07D 211/60

[52] U.S. Cl. ................ 546/215; 546/225; 546/228

[58] Field of Search ................ 546/225, 215, 546/228

[56] References Cited

U.S. PATENT DOCUMENTS 5,227,389  7/1993  Ask et al. ............... 514/330
5,360,805  11/1994  Ask et al. ............... 514/316

*Primary Examiner*—C. Warren Ivy
*Assistant Examiner*—Raymond Covington
*Attorney, Agent, or Firm*—Michael A. Sanzo; Vinson & Elkins

[57] ABSTRACT

The present invention discloses a new and improved process for the preparation of sameridine and its pharmaceutically acceptable salt.

18 Claims, No Drawings

PROCESS FOR THE PREPARATION OF SAMERIDINE

FIELD OF THE INVENTION

The present invention is directed to a new and improved process for the preparation of sameridine and its hydrochloride salt.

BACKGROUND AND PRIOR ART

In WO 91/09845 the compound sameridine is disclosed, as well as a process for preparing and using the same. The starting material in the process disclosed in WO 91/09845 is norpetidin, while the starting material in the process according to the present invention is cyanophenylpiperidine, thus providing a substantially different synthetic method, even after the first step.

The process according to the present invention for the preparation of sameridine and its hydrochloride salt is commercially more advantageous than the process known from WO91/09845. The process according to the present invention is also more advantageous from a technical point of view than the process according to WO91/09845. Actually, the products produced by the improved process are used for the same purposes and in the same manner as sameridine prepared by the prior art process.

OUTLINE OF THE INVENTION

The present invention is directed to a new and improved process for preparing sameridine, N-ethyl-N-methyl-1-hexyl-4-phenyl-4-piperidinecarboxamide which is the compound of the formula (I)

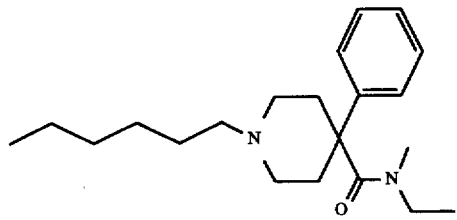

and its hydrochloride salt.

Scheme 1 shows the synthetic route for the preparation of the compound (I) as well as the preparation of the hydrochloride salt of the compound of the formula (I).

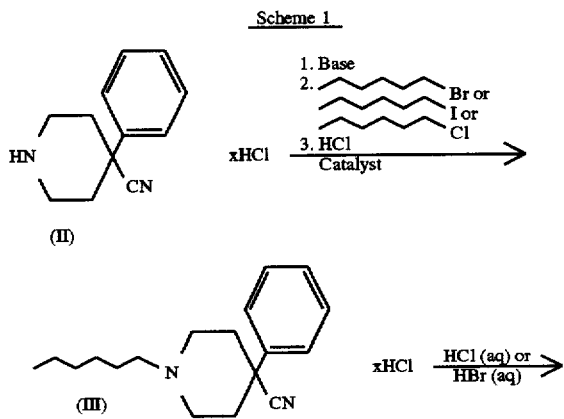

Scheme 1

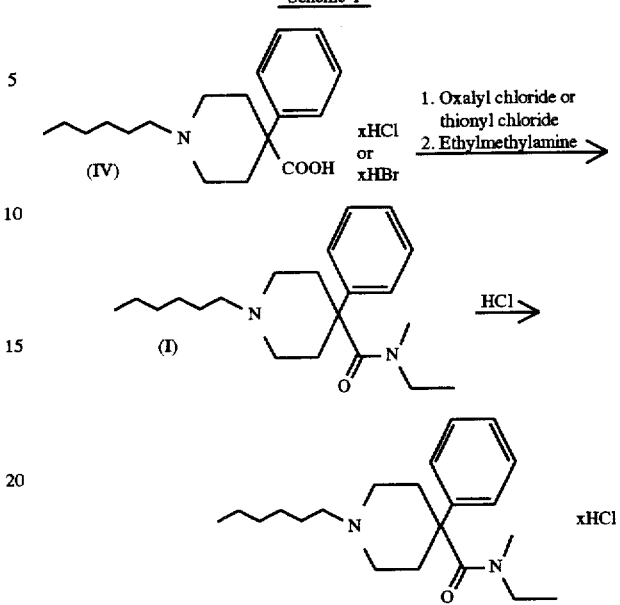

In the process according to the invention the compound (I) is prepared by liberating the starting material 4-cyano-4-phenylpiperidine×HCl from its HCl salt by extraction in an organic solvent with diluted base, whereafter alkylation with 1-bromohexane, 1-iodohexane or 1-chlorohexane takes place in the presence of a base and a catalyst. Optionally the reaction is performed without a catalyst, but results in a more time-consuming reaction.

Examples of bases that can be used in the first reaction step are carbonates such as sodium carbonate and potassium carbonate, or amines, such as triethylamine.

Other possible bases will be appreciated as useful by a person skilled in the art. Preferably, potassium carbonate is used.

The organic solvent can be selected from isobutyl methylketone, acetonitrile, ethanol, butanol and toluene. However, other suitable organic solvents are useful, as would be appreciated by a person skilled in the art.

The optional catalyst employed is an iodide catalyst, preferably sodium iodide.

The reaction is completed by heating to reflux temperature, and the inorganic salts are removed by extraction with water. The product is precipitated as the HCl salt of the formula (III) and thereafter isolated.

The compound of the formula (III) precipitated as its HCl salt is converted by is reaction in HCl (aq) or HBr (aq). After complete conversion the product of the formula (IV) is crystallized by cooling, and is thereafter isolated.

The compound (IV) in an organic solvent or in mixtures of organic solvents, is reacted with oxalyl chloride followed by reaction with ethylmethylamine. The product (I) is washed with water and the solvent is evaporated. The organic solvent includes chlorinated solvents such as methylene chloride or toluene, or mixtures thereof.

The product (I) is thereafter dissolved in an organic solvent and precipitated as a HCl salt, whereafter the product is isolated. Examples of useful organic solvents are ethyl acetate, acetone and methylisobutylketone. The intermediates may be dried or used in moist form.

The purity of the final product of the formula (I) and of its HCl salt respectively, is more than 99% based on GC (gas chromatography) or HPLC (High Performance Liquid Chromatography) analyses.

The NMR spectra of the hydrochloride salt of the product of the formula (I) were obtained from solutions in CDCl$_3$ at room temperature on a Varian Gemini 300 NMR instrument.

DETAILED DESCRIPTION OF THE INVENTION

The invention will now be described in detail by the following examples.

EXAMPLE 1 A

Preparation of 4-Cyano-1-hexyl-4-phenyl-piperidine×HCl (Compound III)

4-Cyano-4-phenylpiperidine×HCl (1.0 kg, 4.5 mol) was treated with isobutyl methyl ketone and NaOH(aq), and to the free base, K$_2$CO$_3$ (0.6–0.9 kg, 4.5–7.0 mol), NaI (0.07–0.10 kg, 0.5–0.7 mol) and 1-bromohexane (0.7–1.2 kg, 4.5–7.0 mol) were added. Thereafter the mixture was heated to reflux temperature in order to complete the reaction. The reaction mixture was washed with H$_2$O and after addition of an equimolar quantity of HCl (aq) to the organic phase, a crystalline product precipitated and was collected, washed with isobutyl methyl ketone, and dried. The yield was about 1.2 kg (95%).

EXAMPLE 1 B

As an alternative to the first step of Example 1A the following simplified procedure was performed.

To 4-Cyano-4-phenylpiperidine×HCl (1.0 kg, 4.5 mol),2 mol of diluted sodium hydroxide was added, followed by NaI (0.07–0.10 kg, 0.5–0.7 mol) and 1-bromohexane (0.7–1.2 kg, 4.5–7.0 mol). The mixture was heated to reflux temperature in order to complete the reaction. The phases were separated and an equimolar quantity of HCl (aq) was added to the organic phase, a crystalline product precipitated and was collected, washed with isobutyl methyl ketone, and dried. The yield was about 1.2 kg (95%).

The result of the $^{13}$C(DMSO) NMR analysis is shown in Table 1.

TABLE 1

Assignments according to the $^{13}$C-spectrum for the compound III (se numbering of the molecule).

| Carbon No. | Shift (ppm) |
|---|---|
| 12 | 13.88 |
| 10,11 | 21.88 |
| 9 | 23.15 |
| 8 | 25.76 |
| 3,5 | 30.68 |
| 4 | 32.54 |
| 6,2 | 49.34 |
| 7 | 55.69 |
| 13 | 120.96 |
| 16,18 | 125.53 |
| 17 | 128.69 |
| 15,19 | 129.34 |
| 14 | 138.53 |

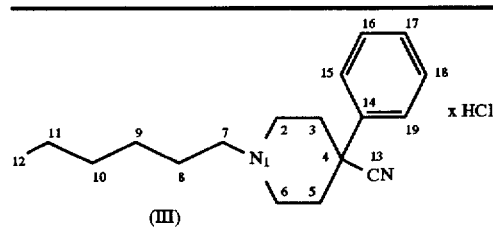

(III)

EXAMPLE 2

Preparation of 1-hexyl-4-phenyl-4-piperidine carboxylic acid×HCl (Compound IV)

The product of Example 1 (1.2 kg, 4.0 mol) was heated to reflux temperature in HCl (aq). After complete conversion and cooling, the crystalline product was collected and washed. The yield, calculated on the dry basis, was about 0.96 kg (80%).

The result of the $^{13}$C(DMSO) NMR analysis is shown in Table 2.

TABLE 2

Assignments according to the $^{13}$C-spectrum for the compound IV (se numbering of the molecule).

| Carbon No. | Shift (ppm) |
|---|---|
| 12 | 13.90 |
| 10,11 | 21.91 |
| 9 | 23.17 |
| 8 | 25.83 |
| 3 | 30.52 |
| 5 | 30.71 |
| 4 | 47.45 |
| 2,6 | 49.88 |
| 7 | 55.67 |
| 16,18 | 125.48 |
| 17 | 127.48 |
| 15,19 | 128.79 |
| 14 | 142.00 |
| 13 | 174.19 |

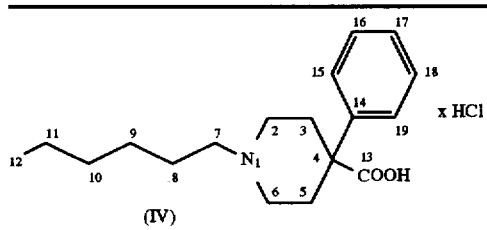

(IV)

EXAMPLE 3

Preparation of N-ethyl-1-hexyl-N-methyl-4-phenyl-4-piperidine-carboxamide (Compound I)

To the product of Example 2(0.96 kg, 2.9 mol), mixed with toluene, oxalyl chloride (0.7–4.3 kg, 5.8–34.0 mol) was added. The mixture was heated to 50° C. to complete the conversion and the excess of oxalyl chloride was removed by evaporation. Toluene and ethylmethylamine (0.3–0.8 kg, 5.8–14.5 mol) were added and the mixture was heated again, to 40° C. After completion of the reaction the mixture was washed with water and the organic phase was evaporated, giving a yield of about 0.96 kg (100%).

EXAMPLE 4

Preparation of N-ethyl-1-hexyl-N-methyl-4-phenyl-4-piperidine carboxamide×HCl (Product (I) in its hydrochloride form)

The product of Example 3 (0.96 kg, 2.9 mol) was dissolved in ethyl acetate and an equimolar amount of HCl (aq) was added. The excess of water was removed azeotropically and the precipitated product was collected after cooling, washed with ethyl acetate and dried to constant weight. The yield was about 0.75 kg (44% calculated on 4-cyano-4-phenylpiperidine×HCl), and the purity was more than 99% based on GC or HPLC analyses.

The result of the $^{13}$C(CDCl) NMR analysis is shown in Table 3.

TABLE 3

Assignments according to the $^{13}$C-spectrum for the product I in its hydrochloride form (se numbering of the molecule on next page):

| Carbon No. | Shift (ppm) |
|---|---|
| 16 | 11.33,11.95 |
| 12 | 13.68 |
| 11 | 22.15 |
| 8 | 23.31 |
| 9 | 26.26 |
| 10 | 30.85 |
| 3,5 | 32.13,32.55 |
| 14 | 33.52,35.75 |
| 15 | 44.11,44.31 |
| 4 | 47.87 |
| 2,6 | 50.04 |
| 7 | 57.25 |
| 19 | 124.55 |
| 20 | 127.22 |
| 18 | 129.23 |
| 17 | 142.18 |
| 13 | 171.99,172.38 |

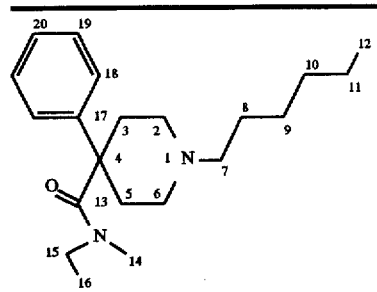

Reprocessing

The product of Example 3 or Example 4, to the extent it fails to comply with any applicable specifications for purity etcetera, may be reprocessed.

The product of Example 3 or the free base extracted from Example 4 is dissolved in a solvent (eg. diisopropyl ether) and is treated with active aluminium oxide. The filtered solution is thereafter evaporated and the product of Example 4 is precipitated according to Example 4.

We claim:

1. A process for the preparation of a compound of the formula (I)

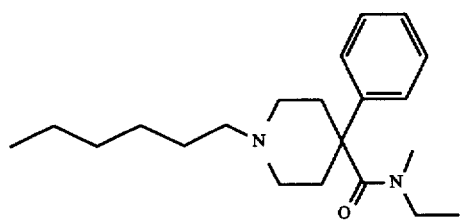

and optionally its hydrochloride salt, comprising i) liberation of 4-cyano-4-phenylpiperidine×HCl of the formula (II)

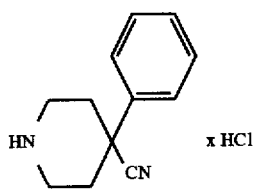

from its HCl salt and thereafter alkylation with 1-bromohexane, 1-iodohexane or 1-chlorohexane in the presence of a base and optionally a catalyst to yield the compound of the formula (III)

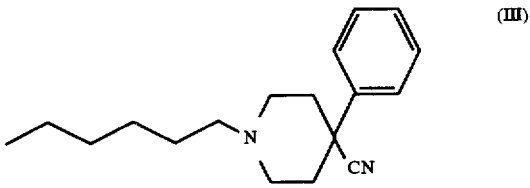

ii) converting the formula (III) compound by heating to reflux temperature to give the compound of the formula (III) precipitated as the corresponding HCl salt of the formula (III); and iii) converting the compound of the formula (III) precipitated as the corresponding HCl salt, by heating to reflux temperature in HCl (aq) or HBr (aq), giving the compound (IV);

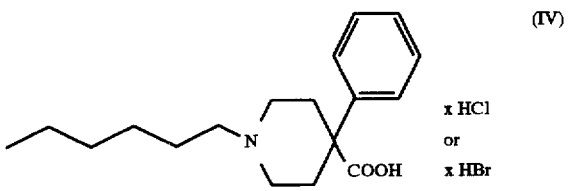

iv) and reacting the compound of the formula (V) with oxalylchloride or thionylchloride, and with ethylmethylamine, to give the compound of the formula (I), which if desired is dissolved and precipitated as the HCl salt.

2. A process according to claim 1, whereby a catalyst is used in step i).

3. A process according to claim 1, whereby the base in step i) is a diluted base.

4. A process according to step ii) of claim 1, further characterized in that inorganic salts are removed by extraction with water.

5. A process according to claim 1, whereby the compound (I) is dissolved in an organic solvent and precipitated as a HCl salt, isolated and dried, giving the second final product being the hydrochloride salt of the formula (I), i.e.

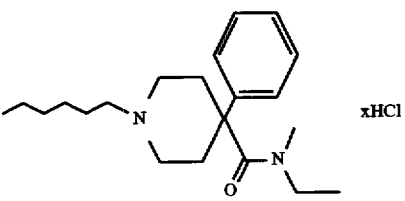

6. A process according to claim 1, whereby the liberation of the HCl salt in step i) is extraction and the organic solvent used for the extraction of step i) is selected from isobutyl methylketone, acetonitrile, ethanol, butanol, and toluene.

7. A process according to claim 6, whereby the organic solvent is isobutyl-methylketone.

8. A process according to claim 2, whereby the catalyst is an iodide catalyst.

9. A process according to claim 8, whereby the catalyst in step i) of claim 1 is sodium iodide.

10. A process according to claim 1, whereby the base in step i) is a carbonate or an amine.

11. A process according to claim 10, whereby the base in step i) is potassium carbonate.

12. A process according to claim 1, whereby the alkylation reagent is 1-bromohexane.

13. A process according to claim 1, whereby the reagent for the conversion reaction of step iii) is HCl (aq).

14. A process according to claim 1, whereby the reagent used in step iv) is oxalylchloride.

15. A product of the formula (I) of claim 1, prepared by the process according to claim 1.

16. A product according to claim 15, in form of its hydrochloride salt.

17. The intermediate of the formula (III)

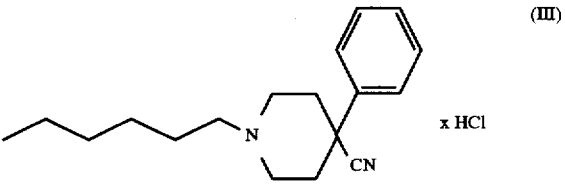

(III)

prepared according to the process of claim 1.

18. The intermediate of the formula (IV)

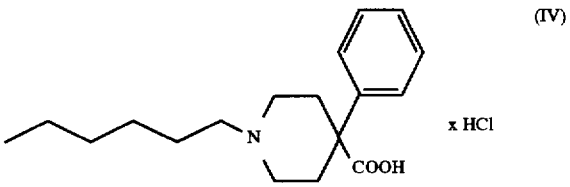

(IV)

prepared according to the process of claim 1.

* * * * *